(12) United States Patent  
Daniel (10) Patent No.: US 9,061,104 B2  
(45) Date of Patent: Jun. 23, 2015

(54) MEDICAMENT INJECTION DEVICE (75) Inventor: Mattias Daniel, Stockholm (SE)

(73) Assignee: SHL Group AB, Nacka Strand (SE)

( * ) Notice: Subject to any disclaimer, the term of this patent is extended or adjusted under 35 U.S.C. 154(b) by 464 days.

(21) Appl. No.: 13/583,626

(22) PCT Filed: Feb. 1, 2011

(86) PCT No.: PCT/SE2011/050101
§ 371 (c)(1),
(2), (4) Date: Oct. 10, 2012

(87) PCT Pub. No.: WO2011/112136
PCT Pub. Date: Sep. 15, 2011

(65) Prior Publication Data
US 2013/0144218 A1 Jun. 6, 2013

Related U.S. Application Data (60) Provisional application No. 61/311,817, filed on Mar. 9, 2010.

(30) Foreign Application Priority Data

Mar. 9, 2010 (SE) ........................ 1050217

(51) Int. Cl.
*A61M 5/32* (2006.01)
*A61M 5/20* (2006.01)
(Continued)

(52) U.S. Cl.
CPC ........... *A61M 5/3202* (2013.01); *A61M 5/3243* (2013.01); *A61M 5/2033* (2013.01);
(Continued)

(58) Field of Classification Search
CPC ... A61M 5/3202; A61M 5/3254; A61M 5/32; A61M 5/326; A61M 5/24; A61M 5/3257; A61M 5/31511; A61M 5/2455; A61M 5/2466; A61M 5/2033; A61M 5/3272; A61M 5/347; A61M 2005/3254; A61M 2005/2403; A61M 2005/2013

USPC ........ 604/187–188, 192, 197–198, 232–237, 604/239–241, 263; 206/365

See application file for complete search history.

(56) References Cited

U.S. PATENT DOCUMENTS

| 5,928,205 | A | 7/1999 | Marshall |
| 2005/0261634 | A1* | 11/2005 | Karlsson ....................... 604/197 |
| 2006/0270984 | A1 | 11/2006 | Hommann |
| 2007/0100290 | A1 | 5/2007 | Schiffmann et al. |

FOREIGN PATENT DOCUMENTS

EP 0824923 A1 2/1998

OTHER PUBLICATIONS

Swedish Patent Office, Int'l Search Report in PCT/SE2011/050101, Jun. 9, 2011.
(Continued)

*Primary Examiner* — Theodore Stigell
*Assistant Examiner* — Tiffany Legette
(74) *Attorney, Agent, or Firm* — Piedmont Intellectual Property (57) ABSTRACT

A medicament delivery device comprising a housing, a tubular activation member, a first resilient member, a container holder, a medicament container (80), a tubular operation member (100), a plunger rod (90), a delivery member; wherein the container is a cartridge, having a membrane (82) and in that the delivery member comprises a retainer member (70) fixedly connected to the container holder, a hub (60) coaxially movable within the retainer member, a needle having opposite proximal and distal ends, and a cap (10) interactively connected to the hub and to the retainer member, wherein the cap comprises a distal end surface abutting with the proximal end surface of the annular contact member such that said hub may be distally moved whereby the needle penetrates the membrane and the cap is detached from the retainer member, allowing the tubular activation member to be moved its activated position.

12 Claims, 9 Drawing Sheets

(51) Int. Cl.
*A61M 5/24* (2006.01)
*A61M 5/34* (2006.01)
(52) U.S. Cl.
CPC .............. *A61M 5/24* (2013.01); *A61M 5/2466* (2013.01); *A61M 5/326* (2013.01); *A61M 5/3272* (2013.01); *A61M 5/347* (2013.01); *A61M 2005/2013* (2013.01)

(56) References Cited

OTHER PUBLICATIONS

Swedish Patent Office, Written Opinion in PCT/SE2011/050101, Jun. 9, 2011.

* cited by examiner

MEDICAMENT INJECTION DEVICE

TECHNICAL FIELD

The present invention relates to a medicament delivery device and in particular to a device where sterile aspects of handling delivery members have been improved and the handling of the device has been facilitated.

BACKGROUND ART

Many medicament delivery devices are developed for self-administration, i.e. the user performs the delivery. This requires a delivery device which is as safe and easy to handle as possible.

In order to meet the requirements, the risk of human errors must be minimized, the number of actions needed to be performed in order to receive a dose need to be reduced and the device must be intuitive and ergonomic to use.

In order to minimize the risk of human errors, it is desirable to have the device as pre-assembled as possible.

One solution for keeping the device as pre-assembled as possible is to deliver the medicament injection device with a delivery member such as a needle, a nozzle or the like, pre-attached. This solution often causes the rear end of the delivery member to protrude into the interior of the container, which could be a drawback if the medicament reacts with the material of the delivery member when exposed for a period of time. In that respect it would be desirable to have the rear part of the delivery member outside the container until the delivery is to be performed.

WO 2009/150078 A1 discloses an injection device wherein the cartridge is penetrated by the needle upon intention of using the device. The needle is coaxially held by a hub such that the needle is extended both in a proximal and in a distal direction from the hub. The hub is axially movable in relation to and interactively connected to a retainer member. A cap is interactively connected to the retainer member and has protrusions interactively connected with grooves on the outer periphery of the hub, such that when the cap is manually operated, it causes the hub to move in a distal direction such that the distal end of the needle penetrates the container.

To minimize the number of actions needed in order to perform the injection, some devices only need to be pressed against the injection area, without the need of injecting by pressing a button or the like, which causes the needle to penetrate the injection area and the device perform the injection. Thereby, the delivery procedure is reduced by at least one step.

One such device is disclosed in patent document EP 1349590 B describing an injector having a number of features that facilitate the handling of the injector. The penetration and injection is performed manually by simply pressing the proximal end of a needle shield against the delivery area, causing the shield to move in a distal direction, enabling the needle to penetrate the injection area and thereafter initiate the injection process. When the injection is performed the injector is withdrawn whereby a needle shield extracts around the needle in a locked way.

Another aspect of injectors is the human aspect of handling the injection device regarding how it is held during operation. A general aim is to have the patient holding the injector in an ergonomic way that permits penetration and injection in different locations on the body, such as around the waist and also on the backside of the waist and/or in the buttocks of the patient. The patient does not see the injector at those locations and need to be able to hold the injector without having to change grip. By removing the action of pushing a button or the like, the patient is free to hold the device as he desires and feels comfortable.

However, a drawback with needle shield activated devices such as the device in EP 1349590 is the need to use syringes, since the activated shield covers the delivery member and hinders the insertion of delivery members. The need of syringes is a drawback since syringes are more expensive and more difficult to handle than cartridges.

SUMMARY OF THE INVENTION

The aim of the present invention is to provide a medicament injection device that is reliable and easy to use when handling the delivery member and activating the device.

This aim is obtained by the features of the patent claims.

According to a main aspect of the invention the medicament delivery device comprises a tubular housing, having opposite proximal and distal ends, a tubular activation member, slidably and coaxially arranged inside the tubular housing and comprising a proximal annular contact member; a first resilient member arranged at the distal end of the tubular activation member for moving it in a proximal direction from a non-activated position, wherein the annular contact member is in contact with the proximal end of the housing, to an activated position, wherein the annular contact member is at a predetermined distance from the proximal end of the housing; a container holder coaxially arranged within the tubular activation member and fixedly attached to the tubular housing; a medicament container arranged within said container holder housing a slidable stopper; tubular operation member rotatably arranged between the container holder and a tubular extension part at the distal end of the housing and comprising first co-acting means interactively connected to corresponding first co-acting means of the tubular activation member; a plunger rod and a second resilient member, wherein the proximal end of said plunger rod is in contact with the stopper and comprising second co-acting means interactively connected to corresponding second co-acting means of the tubular operation member; and a delivery member; wherein the container is a cartridge, having a membrane and in that the delivery member comprises a retainer member fixedly connected to the container holder, a hub coaxially movable within the retainer member, a needle having opposite proximal and distal ends and being fixedly attached to the hub, and a cap interactively connected to the hub and to the retainer member, wherein the cap comprises a distal end surface abutting with the proximal end surface of the annular contact member such that when said cap is manually operated, the hub is distally moved whereby the distal end of the needle penetrates the membrane and the cap is detached from the retainer member, allowing the tubular activation member to be moved by the force from the first resilient member from its non-activated position to its activated position.

According to another aspect of the invention the first co-acting means are at least one inwards extending protrusion on the distal end of the inner surface of the tubular activation member and at least one groove on an outer surface of the tubular operation member, such that said radially inwards extending protrusion is adapted to be guided within the at least one groove forcing the tubular operation member to rotate when the tubular activation member is axially moved.

According to yet another aspect of the invention the second co-acting means are at least one ledge on an inner surface of the tubular operation member and at least one protrusion on an outer surface of the plunger rod, such that said at least one protrusion is abutting said at least one ledge for holding the plunger rod and the second resilient member in a pre-tensioned state.

According to a further aspect of the invention the device further comprises locking means interactively connected to the tubular activation member.

According to yet a further aspect of the invention the locking means is a flexible tongue on the at least one groove of the tubular operation member which locks the radially inwards extending protrusion when said radially inwards extending protrusion is moved over the tongue.

According to another aspect of the invention the hub comprises first coupling means interactively connected to corresponding first coupling means of the retainer member, and second coupling means interactively connected to corresponding second coupling means of the cap.

According to yet another aspect of the invention the cap further comprises third coupling means interactively connected to corresponding third coupling means of the retainer member.

The device according to the present invention presents a number of advantages.

By having the device preassembled, without the needle penetrating the membrane at the initial state, unnecessary problems relating to reactions between the medicament and the material of the delivery member, when exposed for a period of time, are avoided.

There is a high degree of functionality and automation, which remove unnecessary actions for injecting medicament, since the activation of the injector, comprising both penetration and injection is enabled by the needle shield when pushing the injector against the injection site. This causes the needle shield to slide in a distal direction, whereby the needle penetrates the injection site and the medicament is automatically injected at the injection site.

An important safety aspect is met since, during withdrawal, the needle shield is pushed out and covers the needle, and also locks in the extended state, thereby preventing unintentional needle sticks.

Also, cartridges can be used in the device, instead of syringes. Since cartridges are cheaper and easier to get from pre-filling companies, the use of cartridges is preferred.

A reliable and functional injector is provided where the needle shield is held with the compression spring in a tensioned state when delivered to the user, whereby no additional operations, apart from removing a protection cap, need to be performed in order to have the injector ready for injection.

These and other aspects of and advantages with the present invention will become apparent from the following detailed description and from the accompanying drawings.

BRIEF DESCRIPTION OF FIGURES IN THE DRAWINGS

In the following detailed description of the invention, reference will be made to the accompanying drawings, of which

DETAILED DESCRIPTION OF THE INVENTION

In the present application, when the term "distal part/end" is used, this refers to the part/end of the medicament injection device, or the parts/ends of the members thereof, which is/are located the furthest away from the medicament injection site of the patient. Correspondingly, when the term "proximal part/end" is used, this refers to the part/end of the medicament injection device, or the parts/ends of the members thereof, which, is/are located closest to the medicament injection site of the patient.

Figure 1:
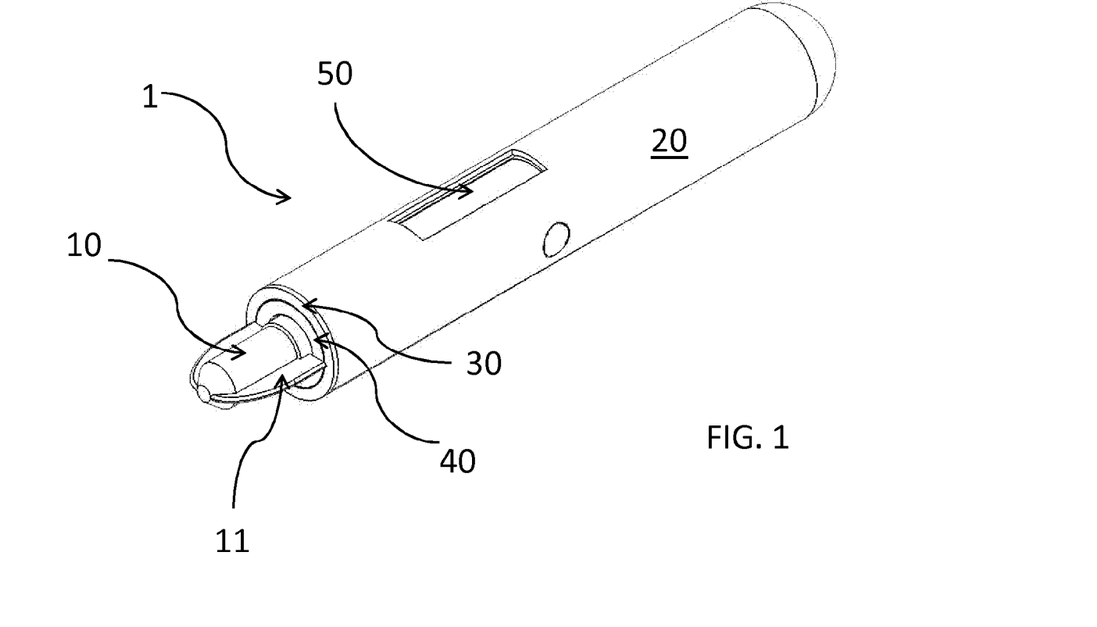
FIG. 1 shows an initial, non-activated, state of the medicament injection device having a cap.
Figure 2:
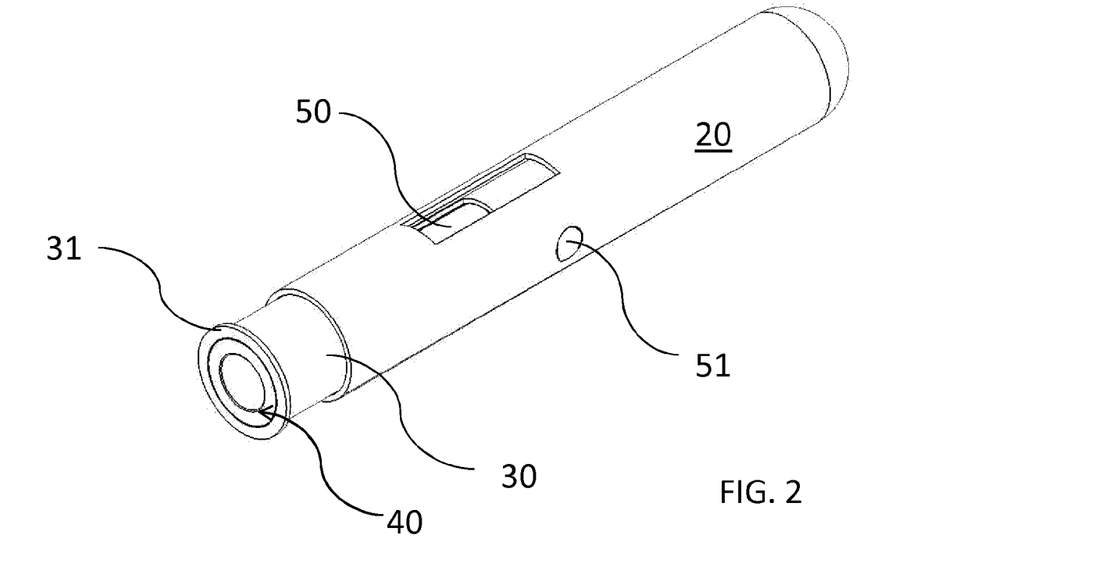
FIG. 2 shows an activated state of the medicament injection device, where the cap is removed.
Figure 3:
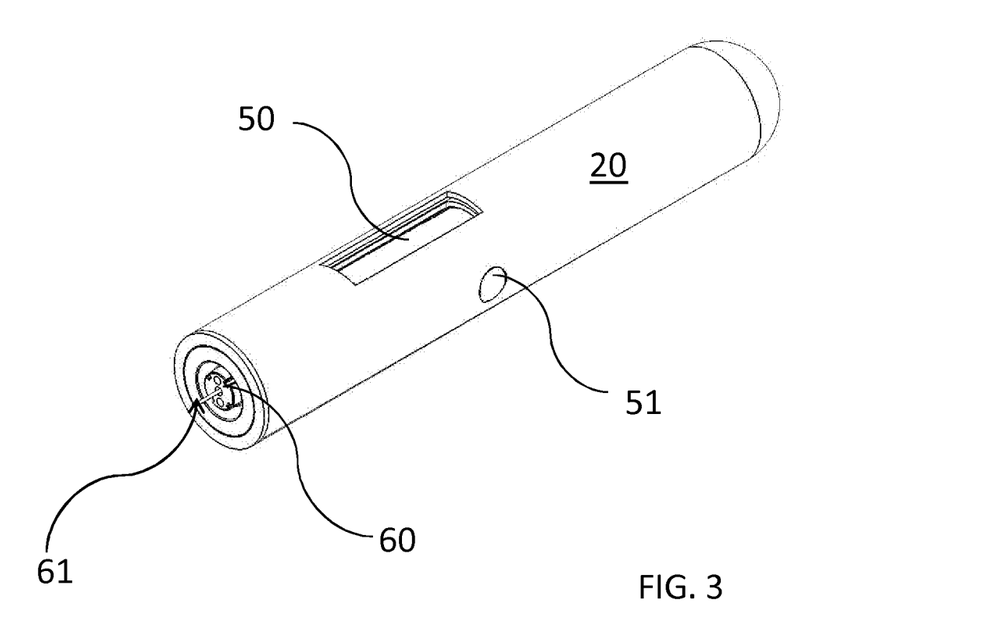
FIG. 3 shows the penetration and injection state of the medicament injection device.

FIGS. 1-3 show simplified perspective views of the medicament injection device 1 according to the present invention, where FIG. 1 shows an initial, non-activated, state of the medicament injection device having a cap 10; FIG. 2 shows an activated state of the medicament injection device, where the cap is removed, and FIG. 3 shows the penetration and injection state of the medicament injection device.

With references to FIGS. 1-3 the medicament delivery device 1 comprises a tubular housing 20, having opposite proximal and distal ends, a tubular activation member 30, slidably and coaxially arranged inside the tubular housing 20 and comprising a proximal annular contact member 31, a first resilient member 34 (see FIG. 9) arranged at the distal end of the tubular activation member 30 for moving it in a proximal direction from a non-activated position, wherein the annular contact member 31 is in contact with the annular proximal end of the housing 20, to an activated position, wherein the annular contact member 31 is at a predetermined distance from the annular proximal end of the housing 30.

The medicament delivery device 1 further comprises a container holder 50 coaxially arranged within the tubular activation member 30 and fixedly attached to the tubular housing 20 via radial extensions 51 protruding through corresponding openings 24 in the housing 20, a medicament container 80 (see e.g. FIGS. 7 and 8a) arranged within the container holder 50, housing a slidable stopper 83 (see FIGS. 8a-8c), a tubular operation member 100 comprising first co-acting means interactively connected to corresponding first co-acting means of the tubular activation member 30, drive means comprising second co-acting means interactively connected to corresponding second co-acting means of the tubular operation member, and a delivery member.

The medicament container is a cartridge, having a membrane 82 (see FIGS. 7, 8a-8c).

The delivery member comprises a retainer member 70 (see FIGS. 7 and 13) fixedly connected to the container holder 50, a hub 60 coaxially movable within the retainer member 70, a needle having opposite proximal and distal ends 61, 64 and being fixedly attached to the hub 60, and a cap 10 interactively connected to the hub 60 and to the retainer member 70.

The cap 10 comprises an annular distal end surface abutting with the annular proximal end surface of the annular contact member 31 of the tubular activation member 30 such that when the cap 10 is manually operated, the hub 60 is distally moved whereby the distal end of the needle 64 penetrates the membrane 82 and when the cap 10 is detached from the retainer member 70, it allows the tubular activation member 30 to be moved by the force from the first resilient member 34 from its non-activated position (FIG. 1) to its activated position (FIG. 2).

Now the medicament delivery device 1 is ready for use. When the user is about to make the injection he/she presses the proximal end, i.e. the annular contact member 31, against the skin. The tubular activation member 30 is then moved in the distal direction in relation to the tubular housing 20 and during the relative movement the needle manually penetrates the skin. When the tubular activation member 30 is about to reach its most distal position in relation to the tubular housing 20 the injection is made, i.e. when the tubular activation member 30 passes by a predetermined injection position close to its most distal position, the injection state is achieved. This penetration and injection state is shown in FIG. 3.

After the injection is made the user removes the device from the skin thereby allowing the tubular activation member 30 to move in the proximal direction in relation to the tubular housing 20 by the force exerted by the first resilient member 34 to reach the final state, the locked state. In the locked state the tubular activation member 30 once more is in its most proximal position as illustrated by FIG. 2. In this state the proximal part of the tubular activation member 30 fully protects the proximal needle end 61 and the tubular activation member 30 is also locked in that position in order to prevent unintentional availability of the proximal needle end 61.

Figure 4:
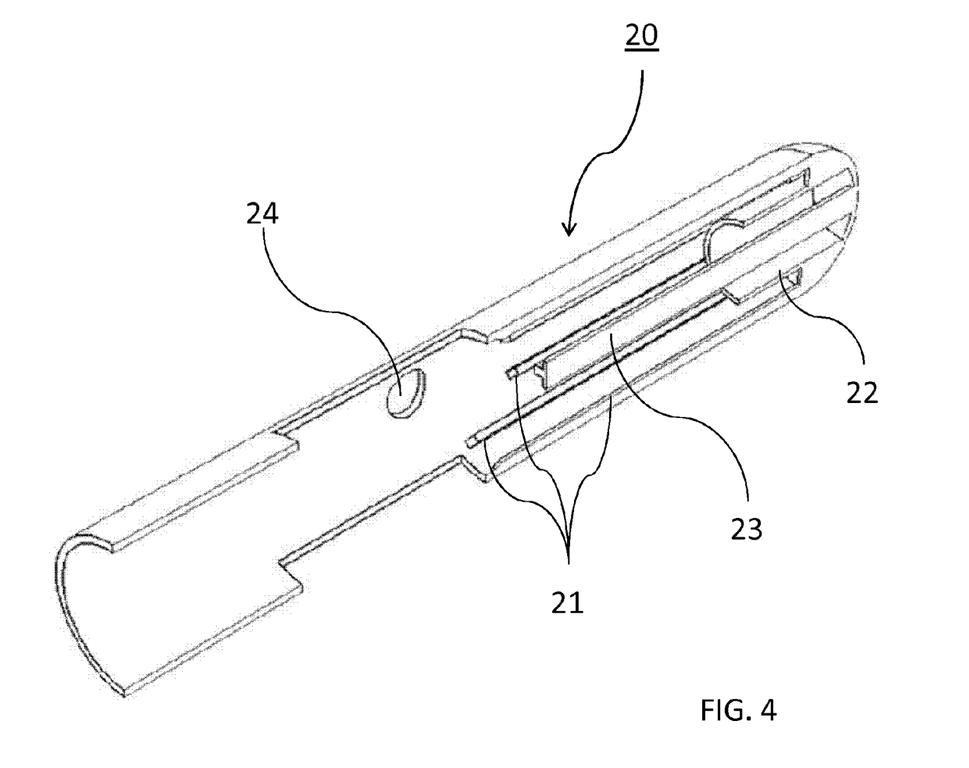
FIG. 4 is a view of the tubular housing in cross-section.

FIG. 4 is a perspective view of the tubular housing 20 in cross-section where a tubular extension part 22 is shown at the distal end of the tubular housing 20. The tubular housing is also provided with openings 24 adapted to cooperate with the radial extensions 51 of the container holder 50 to fixedly hold the container holder in relation to the tubular housing 20. Furthermore, longitudinal interior guiding rods 21, 23 arranged to guide the tubular activation member 30 (not shown).

The tubular operation member 100 (see FIGS. 9-11) is rotatably arranged between the container holder 50 and the tubular extension part 22 at the distal end of the tubular housing 20.

Figure 5:
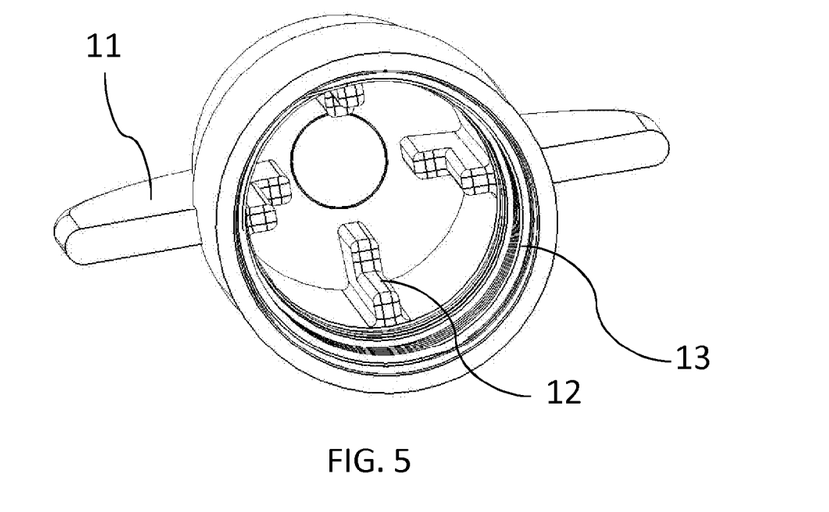
FIG. 5 is a perspective view of the cap seen from its distal end.

FIG. 5 is a perspective view of the cap 10 seen from its distal end. The cap 10 comprises at least two radially outward extending turning members 11, preferably two wing-like members, provided for enabling a user-friendly and easy grip of the cap when turning off the cap in order to activate the medicament delivery device. A further purpose of the turning members 11 is to prevent the tubular activation member 30, by being in contact with the annular contact member 31, from moving in the proximal direction. As an alternative, the cap may be provided with an increased cross-sectional diameter in the section of the cap arranged proximally the tubular activation member.

Figure 6:
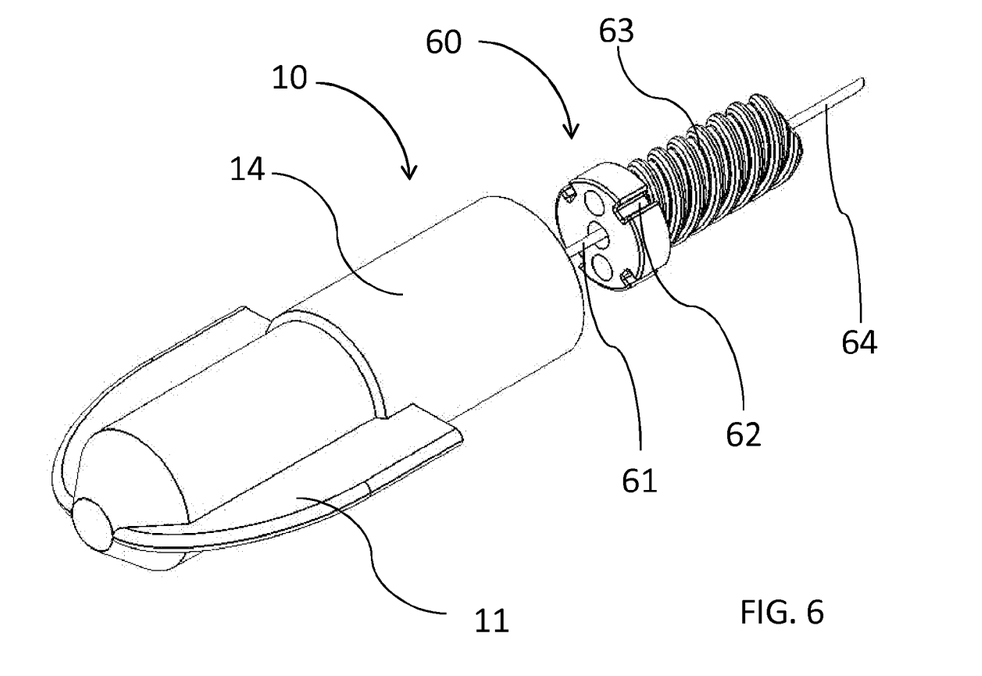
FIG. 6 shows a perspective view of the cap and the hub according to the present invention.

FIG. 6 shows a perspective view of the cap and the hub where the hub 60, provided with the needle 61, 64, comprises first coupling means 63, e.g. in the form of threads on outer surface of the hub, adapted to be interactively connected to corresponding first coupling means 71 (see e.g. FIGS. 7 and 13) of the retainer member 70. The hub also comprises second coupling means 62, e.g. in the shape of radial recesses in the proximal end of the hub, interactively connected to corresponding second coupling means 12 (FIG. 5), e.g. in the shape of radial inward extensions, of the cap 10. In the figures the number of second coupling means 12, 62 is four. However, the number of coupling means 12, 62 is optional as long the intentional function is achieved, i.e. to transfer a rotational movement from the cap to the hub and at the same time allowing the hub to move in the distal direction.

Figure 7:
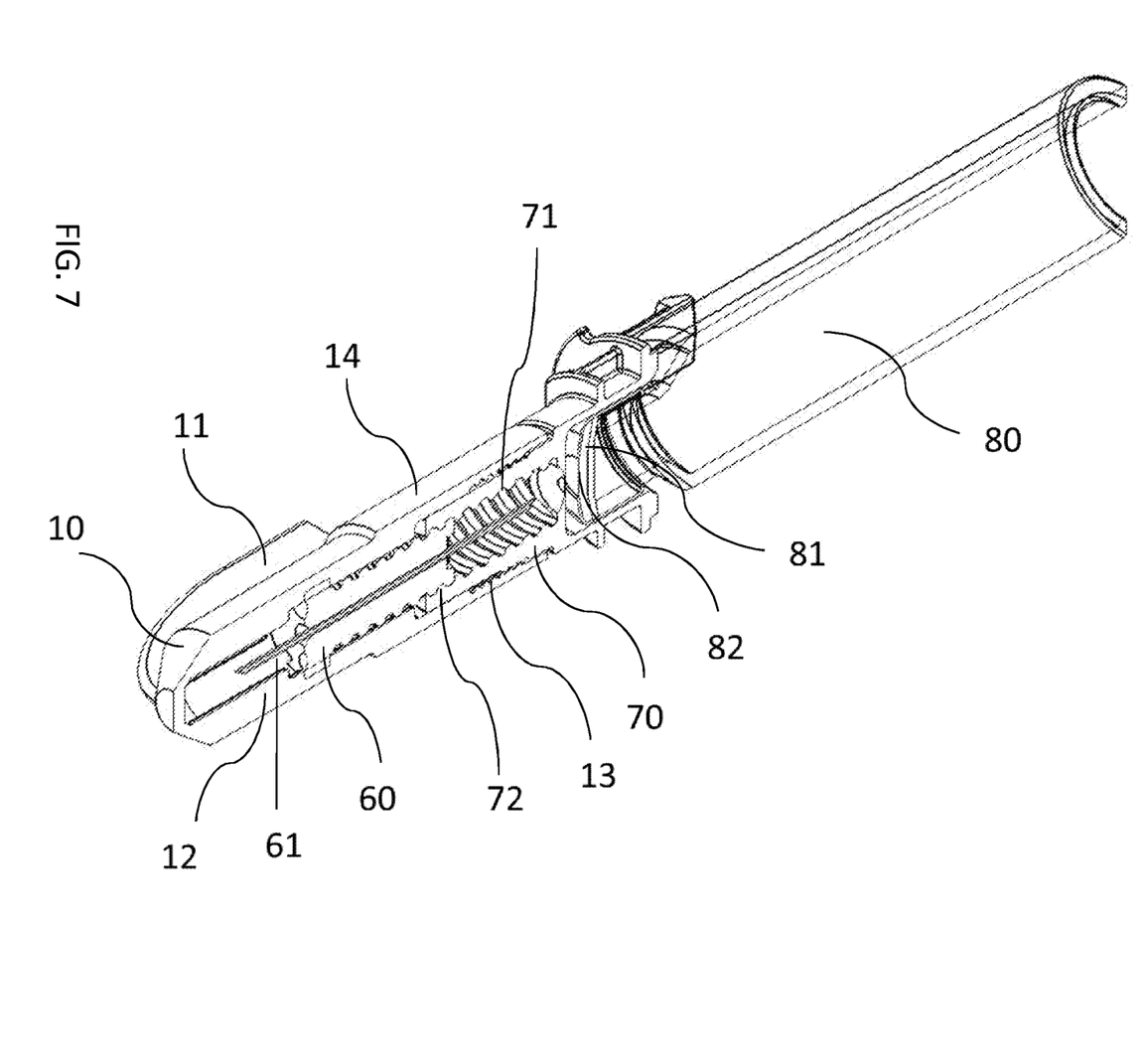
FIG. 7 shows the initial state of the proximal parts of the medicament delivery device in cross-section.
Figure 13:
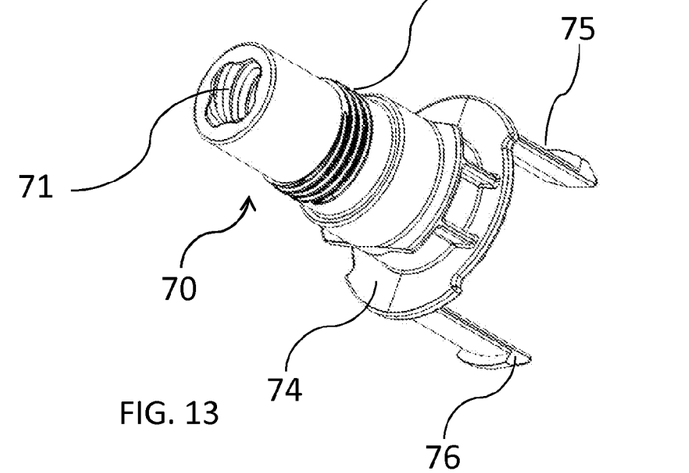
FIG. 13 shows a perspective view of retainer member comprised in the present invention.

The cap 10 further comprises third coupling means 13 (FIG. 5), e.g. in the shape of internal threads, interactively connected to corresponding third coupling means 73 of the retainer member 70 (see FIGS. 7 and 13). The third coupling means 13 is arranged at the inner surface of a distally directed outer sheath 14 of the cap having a circular cylindrical shape, and having an inner diameter slightly larger than the outer diameter of the proximal part of the hub 60 and an outer diameter slightly smaller than the inner diameter of an end shield 40 coaxially arranged to the annular contact member 31.

It is, however, to be noticed that the threads between the inner side of the cap 10 and outer side 73 of the retainer member 70, has a different direction of the pitch than the threads 71, 72 between the hub 60 and the inner surface of the retainer member 70.

When the user then starts to turn the cap 10, this turning causes the hub 60 to be distally screwed into the retainer member 70 whereby the pointed distal end of the injection needle 64 penetrates the membrane 82 of the container. Due to the different directions of the pitches, the cap 10 is simultaneously proximally screwed off and released from the threaded connection with the retainer member and may be removed, i.e. the two operations are completed with a single twist of the cap.

Preferably, the pitches of the threads are chosen such that there is a major longitudinal movement of the hub in the distal direction for a small turning angle in order to prevent as much as possible turning or "drilling" of the distal end of the injection needle 64 in the membrane 82. At the same time the pitch of the threads between the cap 10 and the retainer member 70 is preferably chosen such that the user only needs to turn the cap about half a turn in order to perform the operation so as to avoid having to change grip in order to finish the operation.

FIG. 7 shows, in a perspective cross-section, the proximal parts of the medicament delivery device in an initial state. In the figure the main parts are shown, i.e. the cap 10, the hub 60, the retainer member 70 and the medicament container 80, and the membrane or membranes 81, 82.

Figure 8A:
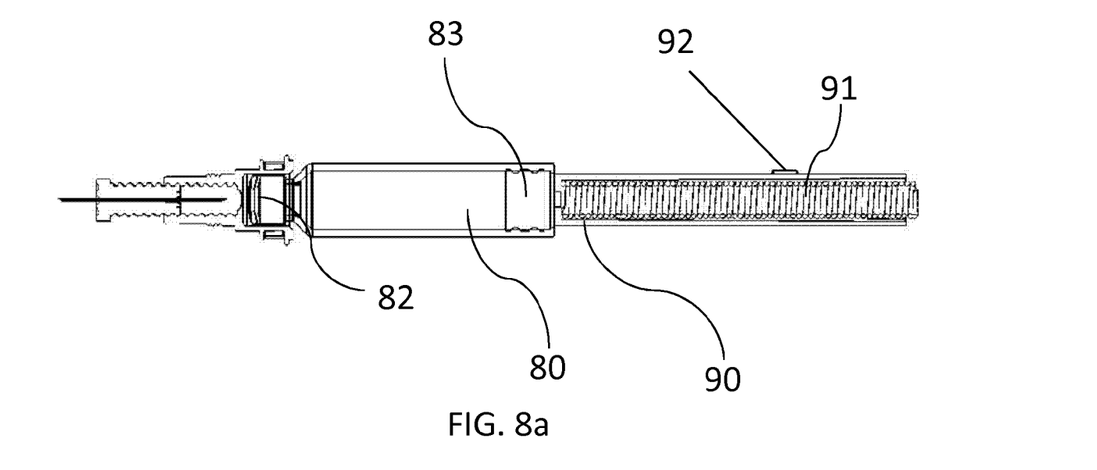
FIG. 8a-c is a sectional view of the interiors of the medicament delivery device according to the present invention from its initial state to its locked state.
Figure 8B:
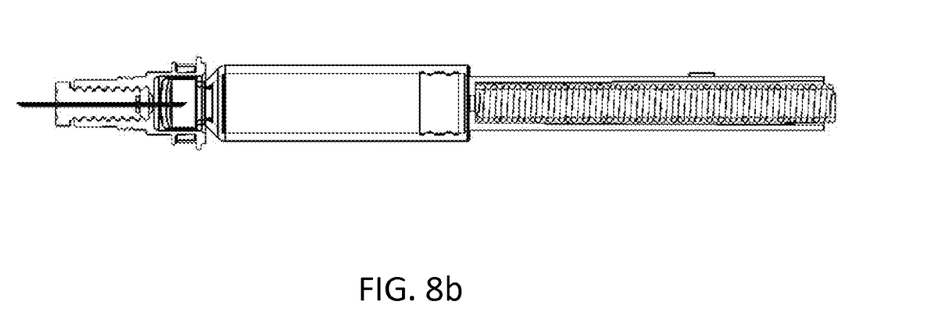
Figure 8C:
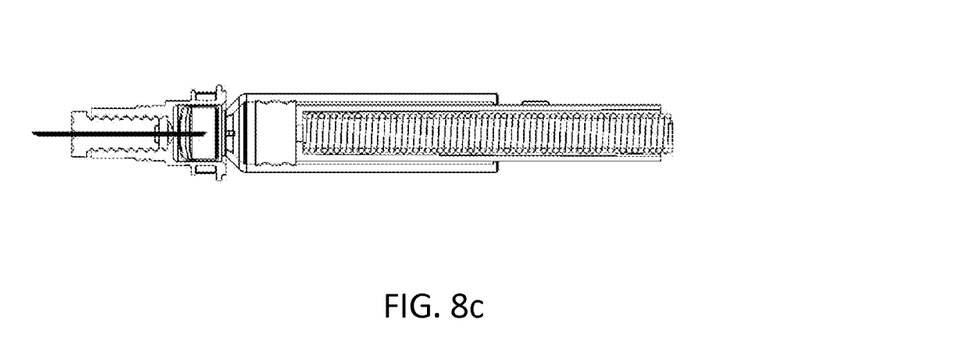

FIGS. 8a-c are sectional views of the interior of the medicament delivery device according to the present invention from its initial state, shown in FIG. 8a, via the state where the needle 64 has penetrated the membrane, i.e. a ready-to-use state, shown in FIG. 8b, to its locked state, i.e. the injection has been made, shown in FIG. 8c. In the figures are shown the medicament container 80, the membrane 82, the stopper 83, a plunger rod 90 enclosing a second resilient member 91 making up the drive means. The proximal end of the plunger rod 90 is in contact with the stopper 83. In the figures are also shown a protrusion 92 at the outer surface of the plunger rod 90 whose function will be discussed below.

Figure 9:
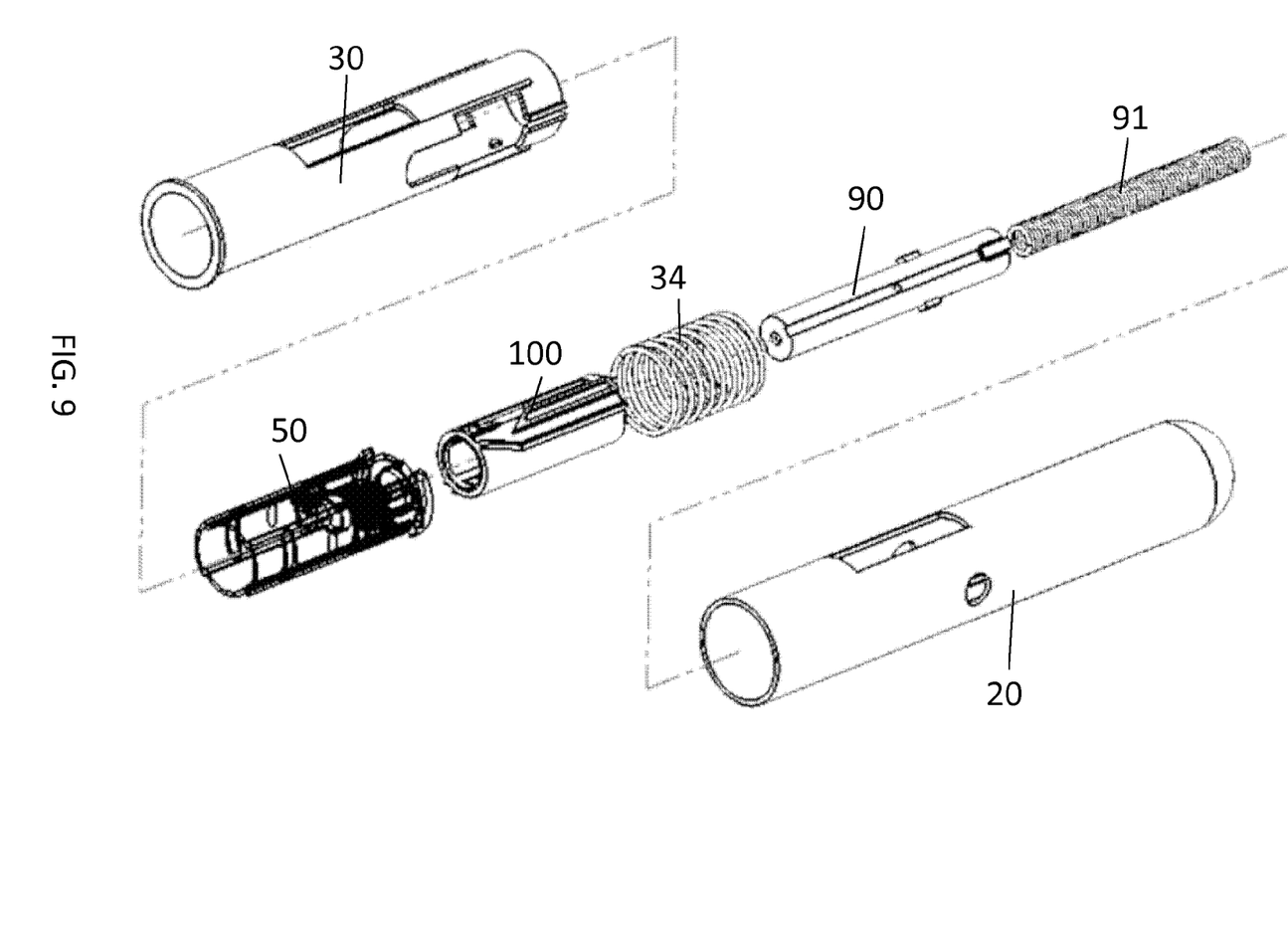
FIG. 9 shows an exploded view of the driving means comprised in the present invention.

FIG. 9 shows an exploded view of the driving means and other means comprised in the present invention, the tubular housing 20, the tubular activation member 30, the first resilient member 34, the container holder 50, the plunger rod 90, the second resilient member 91, and the tubular operation member 100.

Figure 10:
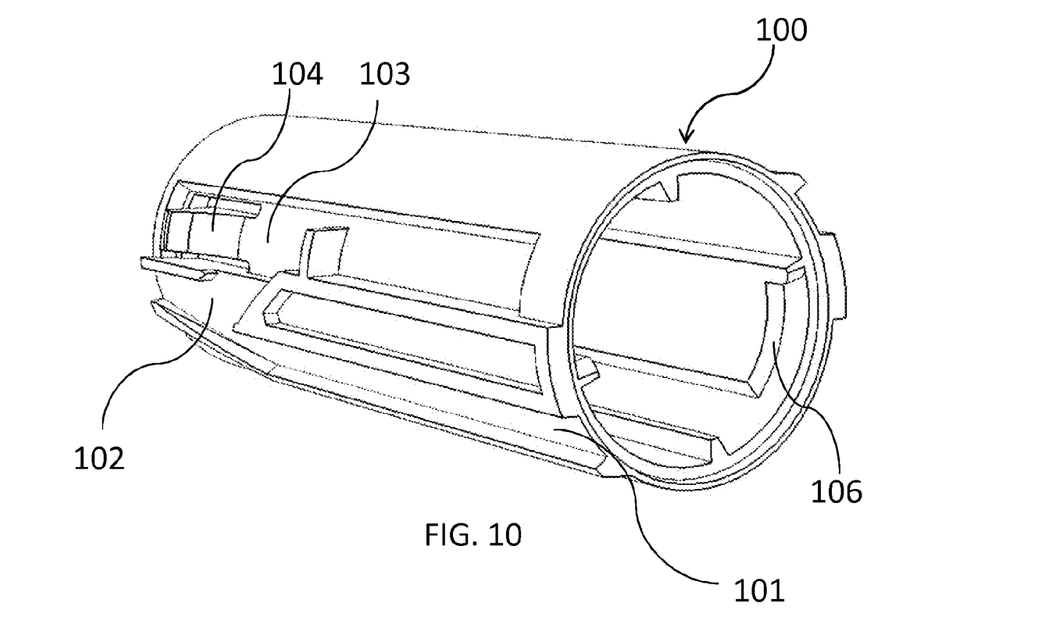
FIG. 10 shows a perspective view of the tubular operation member comprised in the present invention.

FIG. 10 shows a perspective view of the tubular operation member 100, seen from the distal end, comprised in the present invention.

The above-mentioned first co-acting means are at least one inwards extending protrusion 35 (see FIG. 12) on the distal end of the inner surface of the tubular activation member 30 and at least one groove 101, 102, 103 on an outer surface of the tubular operation member 100, such that said radially inwards extending protrusion 35 is adapted to be guided within the at least one groove forcing the tubular operation member 100 to rotate when the tubular activation member is axially moved.

Figure 11:
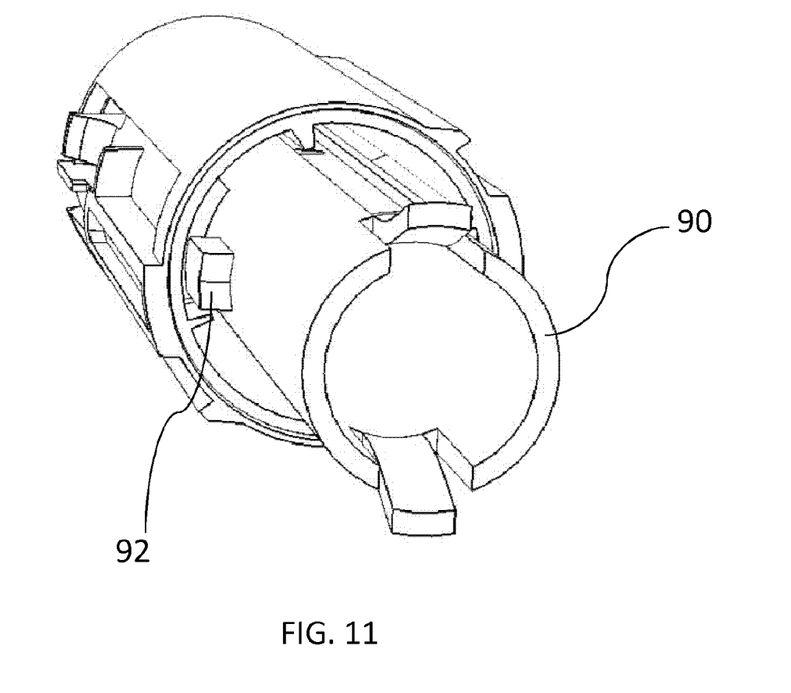
FIG. 11 shows a perspective view of the tubular operation member and the plunger rod comprised in the present invention.

FIG. 11 shows a perspective view of the tubular operation member 100 and the plunger rod 90, seen from the distal end, comprised in the present invention.

The above-mentioned second co-acting means are at least one ledge 106 on an inner surface of the tubular operation member 100 and at least one protrusion 92 on an outer surface of the plunger rod 90, such that said at least one protrusion 92 is abutting said at least one ledge 106 for holding the plunger rod 90 and the second resilient member 91 in a pre-tensioned state.

In a further embodiment the device comprises locking means interactively connected to the tubular activation member 30. The locking means is preferably a flexible tongue 104 (see FIG. 10) on the at least one groove of the tubular operation member 100 which locks the radially inwards extending protrusion 35 when the radially inwards extending protrusion 35 is moved over the tongue 104.

With references mainly to FIGS. 10 and 11 the operation of the device will now be described.

In the pre-tensioned state, the at least one protrusion 92 is abutting the ledge 106 and the protrusion 35 at the inner surface of the tubular activation member 30 is in position 101.

When the cap 10 is removed the activation member 30 is forced in the proximal direction by the first resilient member 34 and the protrusion 35 is moved along the groove from position 101 to position 102 achieving an anticlockwise rotation of the operation member 100 seen from the distal end. The activation member 30 is now in its most proximal position, the distal needle 64 has penetrated the membrane 82 and the medicament delivery device is now ready for use. When the activation member 30 is moved in the distal direction the protrusion 35 is moved along the groove from position 102 to position 103 forcing the tubular operation member 100 to rotate further in the same anticlockwise direction. During the rotation of the tubular operation member 100 the protrusion 92 is moved along the ledge 106 and finally comes off the ledge 106 which enables the release of the tensioned plunger rod 90 to move in the proximal direction, by the force exerted by the second resilient member 91, and to apply a force to the stopper 83 that is forced to move in the proximal direction and the medicament is delivered. When the medicament has been delivered and the medicament delivery device is removed from the skin the tubular activation member 30 is forced in the proximal direction by means of the first resilient member 34 and the locking means, e.g. a flexible tongue 104 (see FIG. 10), on the at least one groove of the tubular operation member 100 which locks the radially inwards extending protrusion 35 when the radially inwards extending protrusion 35 is moved over the tongue 104.

Figure 12:
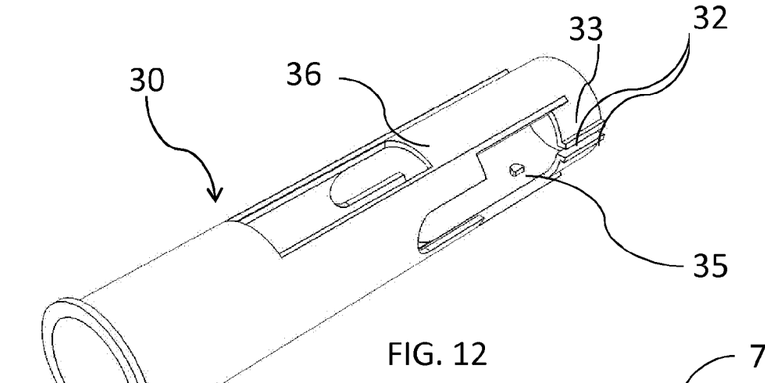
FIG. 12 shows a perspective view of the tubular activation member comprised in the present invention.

FIG. 12 shows a perspective view of the tubular activation member 30 comprised in the present invention. Guiding means 32, 33, 36 are adapted to cooperate with corresponding guiding rods at the interior of the tubular housing 20 (illustrated in FIG. 4) in order to prevent the tubular activation member 30 from rotating in relation to the tubular housing and to allow the tubular activation member to move in the axial direction in relation to the tubular housing.

Figure 14:
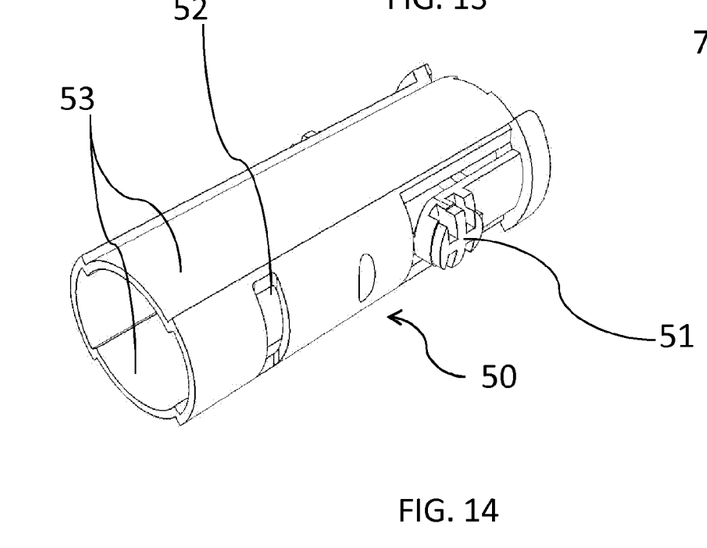
FIG. 14 shows a detailed view of the container holder comprised in the present invention.

FIG. 13 shows a perspective view of the retainer member comprised in the present invention, comprising inner 71 and outer 73 threads and support and attaching means 74, 75 and 76 arranged to fixate the retainer member inside the container holder 50. When the retainer member is fixated the attaching means 75, 76 are held in openings 52 (see FIG. 14) and the support means 74 mates with a corresponding profile 53 (see FIG. 14) of the container holder. Finally, FIG. 14 shows a detailed view of the container holder 50 comprised in the present invention.

It is thus to be understood that the embodiments described above and shown in the drawings are to be regarded only as non-limiting examples of the present invention and that it may be modified within the scope of the patent claims.

The invention claimed is:

1. A medicament delivery device, comprising:
   a tubular housing having opposite proximal and distal ends;
   a tubular activation member slidably and coaxially arranged inside the tubular housing and comprising a proximal annular contact member;
   a first resilient member arranged at the distal end of the tubular activation member for moving the tubular activation member in a proximal direction from a non-activated position, in which the annular contact member is in contact with the proximal end of the housing, to an activated position, in which the annular contact member is at a predetermined distance from the proximal end of the housing;
   a container holder coaxially arranged within the tubular activation member and fixedly attached to the tubular housing;
   a medicament container arranged within the container holder and including a slidable stopper;
   a tubular operation member rotatably arranged between the container holder and a tubular extension part at the distal end of the housing and comprising a first co-acting device interactively connected to a corresponding first co-acting device of the tubular activation member;
   a plunger rod and a second resilient member, wherein a proximal end of the plunger rod contacts the stopper and comprising a second co-acting device interactively connected to a corresponding second co-acting device of the tubular operation member; and
   a delivery member;
   wherein the container is a cartridge having a membrane; the delivery member comprises a retainer member fixedly connected to the container holder, a hub coaxially movable within the retainer member, a needle having opposite proximal and distal ends and being fixedly attached to the hub, and a cap interactively connected to the hub and to the retainer member; the cap comprises a distal end surface abutting the proximal end surface of the annular contact member such that when the cap is manually operated, the hub is distally moved whereby a distal end of the needle penetrates the membrane and the cap detaches from the retainer member, thereby enabling the tubular activation member to be moved by a force from the first resilient member from its non-activated position to its activated position.

2. The medicament delivery device of claim 1, wherein the second co-acting devices include at least one ledge on an inner surface of the tubular operation member and at least one protrusion on an outer surface of the plunger rod, such that the at least one protrusion abuts the at least one ledge for holding the plunger rod and the second resilient member in a pre-tensioned state.

3. The medicament device of claim 1, wherein the hub comprises a first coupling device interactively connected to a corresponding first coupling device of the retainer member, and a second coupling device interactively connected to a corresponding second coupling device of the cap.

4. The medicament device of claim 3, wherein the cap further comprises a third coupling device interactively connected to a corresponding third coupling device of the retainer member.

5. The medicament delivery device of claim 1, wherein the first co-acting devices include at least one inwardly extending protrusion on the distal end of the inner surface of the tubular activation member and at least one groove on an outer surface of the tubular operation member, such that the radially inwardly extending protrusion is configured to be guided within the at least one groove thereby forcing the tubular operation member to rotate when the tubular activation member axially moves.

6. The medicament delivery device of claim 5, wherein the second co-acting devices include at least one ledge on an inner surface of the tubular operation member and at least one protrusion on an outer surface of the plunger rod, such that the at least one protrusion abuts the at least one ledge for holding the plunger rod and the second resilient member in a pre-tensioned state.

7. The medicament device of claim 5, wherein the hub comprises a first coupling device interactively connected to a corresponding first coupling device of the retainer member, and a second coupling device interactively connected to a corresponding second coupling device of the cap.

8. The medicament device of claim 7, wherein the cap further comprises a third coupling device interactively connected to a corresponding third coupling device of the retainer member.

9. The medicament delivery device of claim 1, further comprising a locking mechanism interactively connected to the tubular activation member.

10. The medicament delivery device of claim 9, wherein the locking mechanism includes a flexible tongue on the at least one groove of the tubular operation member which locks the radially inwardly extending protrusion when the radially inwardly extending protrusion moves over the tongue.

11. The medicament device of claim 9, wherein the hub comprises a first coupling device interactively connected to a corresponding first coupling device of the retainer member, and a second coupling device interactively connected to a corresponding second coupling device of the cap.

12. The medicament device of claim 11, wherein the cap further comprises a third coupling device interactively connected to a corresponding third coupling device of the retainer member.

* * * * *